United States Patent [19]

Preidel

[11] Patent Number: 5,746,898
[45] Date of Patent: May 5, 1998

[54] ELECTROCHEMICAL-ENZYMATIC SENSOR

[75] Inventor: Walter Preidel, Erlangen, Germany

[73] Assignee: Siemens Aktiengesellschaft, Munich, Germany

[21] Appl. No.: 973,933

[22] Filed: Nov. 12, 1992

Related U.S. Application Data

[63] Continuation of Ser. No. 742,598, Aug. 8, 1991.

[30] Foreign Application Priority Data

Aug. 10, 1990 [EP] European Pat. Off. ............. 90115421

[51] Int. Cl.$^6$ ...................... G01N 27/327; G01N 27/404
[52] U.S. Cl. ........................ 204/403; 204/412; 204/415; 205/778; 205/783; 435/817
[58] Field of Search ........................ 204/153.12, 153.17, 204/403, 412, 415

[56] References Cited

U.S. PATENT DOCUMENTS

| | | | |
|---|---|---|---|
| 3,539,455 | 11/1970 | Clark | 204/153.12 |
| 3,591,480 | 7/1971 | Neff et al. | 204/403 |
| 4,310,400 | 1/1982 | Mark et al. | 204/418 |
| 4,655,880 | 4/1987 | Liu | 204/1 T |
| 4,711,245 | 12/1987 | Higgins et al. | 204/403 |
| 4,853,091 | 8/1989 | Mund et al. | 204/1 T |
| 4,909,908 | 3/1990 | Ross | 204/403 |

FOREIGN PATENT DOCUMENTS

| | | |
|---|---|---|
| 0127958 | 12/1984 | European Pat. Off. . |
| 0136362 | 4/1985 | European Pat. Off. . |
| 0359831 | 3/1990 | European Pat. Off. . |
| 1167317 | 10/1969 | United Kingdom . |

*Primary Examiner*—T. Tung
*Attorney, Agent, or Firm*—Kenyon & Kenyon

[57] ABSTRACT

An electrochemical-enzymatic sensor for the determination of substances, in particular glucose, in body fluids, which possesses a good long-term stability, includes: a sensor electrode of electrocatalytically inactive carbon, a counterelectrode, a reference electrode, an enzyme-containing layer located before the sensor electrode, and a diaphragm of biocompatible, hydrophilic, oxygen-permeable material covering the enzyme layer toward the body fluid and retaining the enzyme.

15 Claims, No Drawings

ELECTROCHEMICAL-ENZYMATIC SENSOR

This application is a continuation of application Ser. No. 07/742,598 filed Aug. 8, 1991.

BACKGROUND OF THE INVENTION

1. Field of the Invention

The invention relates to an electrochemical-enzymatic sensor for the determination of substances, in particular glucose, in body fluids, as well as to an implantable sensor arrangement.

2. Description of Related Art

Measurement of the glucose concentration in the blood (by means of an implantable sensor) is necessary, for example, in diabetes therapy—for controlling the insulin dosage by means of an implanted pump. For this purpose, a sensor is needed which responds specifically to glucose, has good long-term stability, and is biocompatible. Such a glucose sensor would be usable also in clinical tests for measuring glucose and in glucose tolerance tests, that is, it need not necessarily be implanted.

Determination of glucose in the blood can be done with enzyme sensors, generally with the use of glucose oxidase as the enzyme (see J. G. Schindler "Bioelektrochemische Membranelektroden", published by Walter de Gruyter, Berlin—New York, 1983, pages 211 ff.). A major drawback to the use of enzymatic glucose sensors for diabetes therapy, however, has been the insufficient long-term stability of the sensors. Various measures for stabilizing the enzyme, for example inclusion of the enzyme in a matrix and chemical bonding or adsorption of the enzyme, do indeed lead to improved stability, but also lead to reduced selectivity for glucose. The currently obtainable long-term stability of enzyme sensors, therefore, is generally no more than 30 days in vitro or up to 14 days in vivo, although an implantation period of about 100 days has been reported (see "Nachr. Chem. Tech. Lab.", vol. 38 (1990), pages 868 and 869).

Enzymatic glucose sensors operate on the following principle:

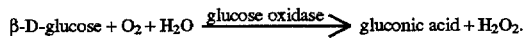

$$\beta\text{-D-glucose} + O_2 + H_2O \xrightarrow{\text{glucose oxidase}} \text{gluconic acid} + H_2O_2.$$

The glucose concentration is determined by a measure of either the oxygen ($O_2$) depletion or the hydrogen peroxide ($H_2O_2$) enrichment. The measuring is done potentiometrically or amperometrically, using a measuring electrode of a noble metal, generally platinum. It seems that the insufficient long-term stability of the enzyme, i.e. the cause of the aging, is due to an effect on the enzyme by the $H_2O_2$ or by the measuring electrode or due to products formed at the measuring electrode by decomposition of the enzyme.

SUMMARY OF THE INVENTION

It is therefore the object of the invention to provide an electrochemical-enzymatic sensor wherein there is no adverse effect on the enzyme by the sensor electrode so that the sensor has a good long-term stability.

According to the invention this is achieved by a sensor having the following characteristics:

a sensor electrode of electrocatalytically inactive carbon a counterelectrode a reference electrode an enzyme-containing layer located before the sensor electrode and a diaphragm of biocompatible, hydrophilic, oxygen-permeable material covering the enzyme layer toward the body fluid and retaining the enzyme.

DETAILED DESCRIPTION OF THE INVENTION

The electrochemical-enzymatic sensor according to the invention is based on the principle of an oxygen sensor, that is, variation of the oxygen content is determined. This variation is predominantly a depletion in $O_2$. The combination of an enzyme reaction with an $O_2$ sensor which does not influence the enzyme and hence does not alter the enzyme activity, results in a high long-term stability. In the sensor according to the invention, the measuring or sensor electrode consists of electrocatalytically inactive carbon. At such an electrode only oxygen is reacted, i.e. reduced, while other reactions are greatly inhibited. Furthermore, the enzyme does not react, that is, it is not altered electrochemically.

Also, in the sensor according to the invention there is no poisoning of the measuring electrode by substances which might diffuse through the diaphragm and enzyme layer to the electrode. Since no harmful electrode reactions take place, the enzyme activity is not reduced by reaction products. Furthermore this sensor requires no additional substances for electron transfser, such as ferrocene and tetracyanoquinodimethane, because oxygen reduction occurs at the sensor electrode.

The sensor according to the invention can be used preferably for the determination of glucose (with glucose oxidase). But the principle on which this sensor is based, the combination of an oxygen sensor with an enzyme reaction which produces or consumes oxygen, can be used also for the determination of other substances. Examples are:

various sugars with a corresponding oxidase, such as galactose with galactose oxidase lactate with lactate oxidase methanol or ethanol with alcohol oxidase cholesterol with cholesterol oxidase uric acid with uricase ascorbic acid with ascorbate oxidase pyruvate with pyruvate oxidase adenosine triphosphate with glucose oxidase/hexokinase and hydrogen peroxide with catalase.

The last-named reaction, the $H_2O_2$ determination, involves the formation of oxygen, i.e. an enrichment.

For the sensor according to the invention, the enzyme can be used either in a dissolved or an immobilized form. Immobilization, can be effected by crosslinkage, for example—together with bovine serum albumin—by means of glutaraldehyde, or by inclusion in a matrix, for example of polyacrylamide. In the case of immobilization, generally some of the enzyme activity is lost, and the useful life is thereby limited. To obtain a higher long-term stability, therefore, catalase can advantageously be added to the enzyme. This is to avoid the enrichment of $H_2O_2$, which may impair the enzyme. In addition, the enzyme can be changed at regular intervals.

The sensor according to the invention has a three-electrode arrangement which is triggered by a pulsed voltage (cf. for example EP-OS 0170998). To this end, two potentials, namely a measuring potential and a so-called recovery potential, are imposed on the measuring or sensor electrode. The dwell time at the measuring potential is small in comparison to the cycle duration. In this way the oxygen consumption is kept very low. The current flowing during the measurement period is evaluated as a measuring signal. The current is advantageously integrated and the charge signal is evaluated. The integral of the current is preferably formed with a time delay. The charge is a measure of the oxygen concentration. For such a pulse method the required power is less than 50 µw. Therefore, the sensor according to the invention is usable as long-term implant.

The electrochemical-enzymatic sensor according to the invention is of relatively simple construction. Besides the actual measuring electrode (called also working electrode), a counterelectrode, a reference electrode and an enzyme, only one diaphragm is required. On the other hand usually two diaphragms are used in known enzyme sensors. One diaphragm separates the enzyme from the surrounding electrolyte and the other diaphragm is disposed directly before the measuring electrode. This diaphragm is usually permeable only for a certain molecule type, so as to obtain an electrode reaction as specific as possible. For such a purpose often a so-called Carrier PVC diaphragm is used, however for implants this is problematical due to the toxicity of the components contained therein.

The diaphragm used in the sensor of the invention consists preferably of cellulose acetate or perfluorosulfonated polytetrafluoroethylene. Polyurethane, for example, may be used alternatively. Generally, this diaphragm, which retains the enzyme while being permeable for oxygen, is biocompatible and hydrophilic, that is, permeable for the substance to be determined. Because of the high sensitivity of the sensor for oxygen, a diaphragm can be selected which has a low coefficient of diffusion for the substance to be determined, such as glucose, for example below $10^{-12}$ m$^2$/s. The coefficient of diffusion for oxygen should be such that on the one hand enough oxygen is available for the enzyme reaction, but on the other hand there is no excess. For the maximum measurable concentration of the substance to be determined, the ratio between oxygen diffusion and diffusion of this substance is determining. This ratio is determined by the nature of the diaphragm, i.e. by the degree of hydrophility.

The thickness of the diaphragm is relatively uncritical, as the response time of the sensor for oxygen is very short. However, for the actual measurement of the respective substance response times of several minutes can be tolerated. In general the diaphragm thickness is 10 to 150 µm.

As material for the sensor electrode advantageously vitreous carbon, pyrographite, sputtered carbon, sputtered graphite, and amorphous hydrogenated carbon (a-C:H) can be used. Preferably, vitreous carbon is employed, in non-activated form, that is, a so-called smooth vitreous carbon electrode is used. The counterelectrode is advantageously made of platinum or activated vitreous carbon. The reference electrode is advantageously an Ag/AgCl electrode.

For implant purposes it is advantageous to use a sensor arrangement with two measuring electrodes, one of which is designed as a sensor electrode with enzyme, the other as a sensor electrode without enzyme. That is, in the second case, for example, a solution which contains no enzyme is taken. With the measurement from pulse to pulse, switching from one electrode to the other takes place; the difference between the signals obtained corresponds to the concentration of the substance to be determined. Such an arrangement is well suited for long-term implantation because signal drift is ruled out. In such an arrangement the two sensors, i.e. the two measuring electrodes, preferably have conjointly a single counterelectrode and a single reference electrode. Such arrangements, suitable for implant purposes, are advantageously designed as disk sensors. But for measurements in the blood, preferably so-called tip electrodes are employed. In such electrodes, for example, a polymer solution containing an enzyme is applied on the tip of the measuring electrode and is covered with a diaphragm layer after drying.

The invention will be explained more specifically with reference to the following practical examples which are to be regraded in an illustrative rather than a restrictive sense.

EXAMPLE

For the tests flow through cells made of polysulfone are used, with a smooth vitreous carbon electrode serving as the working electrode (diameter 5 mm; surface 0.2 cm$^2$). The reference electrode is an Ag/AgCl electrode. As the counterelectrode a platinum electrode (sand blasted) or an electrode of activated vitreous carbon (surface 0.2 cm$^2$) is used.

For determining the concentration of glucose there is used, for example, a sensor where the space between the working electrode and a diaphragm of Nafion, i.e. perfluorosulfonated polytetrafluoroethylene (thickness about 35 µm; diffusion coefficient for glucose 5.9×10$^{-13}$ m$^2$/s, for O$_2$ 20×10$^{-13}$ m$^2$/s) contains 10 µl of an aqueous solution of glucose oxidase (in physiological salt solution or Ringer solution). A Ringer solution containing 10% O$_2$ serves as the electrolyte. The sensor is operated by the pulse method (pulse duration 20 ms, integration 15 to 20 ms, cycle duration 2 s).

At 25° C. well reproducible measurement curves are obtained. With the invention, the decrease of the sensor signal over time is substantially less than with conventional sensors. This is attributable to the fact that the sensor electrode is not poisoned. Comparable results are obtained also at 37° C. in Ringer solution. With the use of defibrinated sheep's blood as electrolyte satisfactory results are also obtained.

If a thicker, i.e. less hydrophilic, diaphragm is used (thickness about 105 µm), the sensitivity is greater because the oxygen diffusion is improved, as compared with a reduced glucose diffusion (diffusion coefficient for glucose: 3.1×10$^{-13}$ m$^2$/s, for O$_2$: 14×10$^{-13}$ m$^2$/s). Such sensors were successfully tested (at 25° C.) over a period of more than 100 days.

For the determination of lactate, for example, a solution of lactate oxidase (10 µl) is located in a corresponding manner directly before the working electrode. In this case the diaphragm consists, for example, of cellulose acetate or nitrate.

The sensor according to the invention may also be constructed in the form of a catheter sensor. For the determination of glucose, for example, a three-electrode arrangement is used, with a vitreous carbon electrode as tip and an insulated Ag/AgCl reference electrode disposed behind it, followed by an insulated Pt counterelectrode. The enzyme glucose oxidase is applied on the working electrode of vitreous carbon by immersing the electrode in a mixture of glucose oxidase solution, bovine serum albumin and glutaraldehyde solution (5%), followed by drying. Subsequently the catheter, including the reference electrode, is immersed in a Nafion solution (5%, isopropanol) to cover the enzyme layer with a hydrophilic diaphragm. Such a diaphragm is obtained, for example, also by means of a solution of polyurethane (10%, N-methylpyrrolidone).

What is claimed is:

1. An electrochemical-enzymatic sensor for use in determining the concentration of glucose and other substances in body fluids, comprising:

an oxygen sensor comprising a sensor electrode means for determining an oxygen content, the sensor electrode means being of an electrocatalytically inactive carbon selected from the group consisting of vitreous carbon, pyrographite, sputtered carbon, sputtered graphite and amorphous hydrogenated carbon;

a counterelectrode;

a reference electrode;

an enzyme-containing layer disposed before the sensor electrode means; and a diaphragm of biocompatible, hydrophilic, oxygen-permeable material covering the enzyme layer and retaining the enzyme.

2. The sensor according to claim 1 wherein the counterelectrode comprises one of platinum and activated vitreous carbon.

3. The sensor according to claim 2 wherein the reference electrode is an Ag/AgCl electrode.

4. The sensor according to claim 2 wherein the enzyme is present in dissolved form.

5. The sensor according to claim 2 wherein the enzyme is present in immobilized form.

6. The sensor according to claim 2 wherein the diaphragm comprises one of cellulose acetate and perfluorosulfonated polytetrafluoroethylene.

7. The sensor according to claim 1 wherein the reference electrode is an Ag/AgCl electrode.

8. The sensor according to claim 7 wherein the diaphragm comprises one of cellulose acetate and perfluorosulfonated polytetrafluoroethylene.

9. The sensor according to claim 7 wherein the enzyme is present in dissolved form.

10. The sensor according to claim 7 wherein the enzyme is present in immobilized form.

11. The sensor according to claim 1 wherein the enzyme is present in dissolved form.

12. The sensor according to claim 1 wherein the enzyme is present in immobilized form.

13. The sensor according to claim 1 wherein the diaphragm comprises one of cellulose acetate and perfluorosulfonated polytetrafluoroethylene.

14. An implantable sensor arrangement comprising a first sensor according to claim 1 and a second sensor having a structure identical to the first sensor, but without enzyme.

15. A sensor arrangement according to claim 14 wherein the two sensors have only one counterelectrode and one reference electrode, conjointly.

* * * * *